US009448232B2

(12) United States Patent
Petrucelli et al.

(10) Patent No.: US 9,448,232 B2
(45) Date of Patent: Sep. 20, 2016

(54) METHODS AND MATERIALS FOR DETECTING C9ORF72 HEXANUCLEOTIDE REPEAT EXPANSION POSITIVE FRONTOTEMPORAL LOBAR DEGENERATION OR C9ORF72 HEXANUCLEOTIDE REPEAT EXPANSION POSITIVE AMYOTROPHIC LATERAL SCLEROSIS

(71) Applicant: Mayo Foundation for Medical Education and Research, Rochester, MN (US)

(72) Inventors: Leonard Petrucelli, Ponte Vedra, FL (US); Peter E. Ash, Boston, MA (US); Tania Gendron, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/162,570

(22) Filed: Jan. 23, 2014

(65) Prior Publication Data
US 2014/0206102 A1   Jul. 24, 2014

Related U.S. Application Data

(60) Provisional application No. 61/756,318, filed on Jan. 24, 2013.

(51) Int. Cl.
*A61K 39/395* (2006.01)
*C07K 16/18* (2006.01)
*G01N 33/53* (2006.01)
*C07K 16/44* (2006.01)

(52) U.S. Cl.
CPC ........... *G01N 33/5308* (2013.01); *C07K 16/44* (2013.01)

(58) Field of Classification Search
None
See application file for complete search history.

(56) References Cited

U.S. PATENT DOCUMENTS

| 4,034,074 | A | 7/1977 | Miles |
| 4,036,945 | A | 7/1977 | Haber |
| 4,098,876 | A | 7/1978 | Piasio et al. |
| 4,233,402 | A | 11/1980 | Maggio et al. |
| 4,331,647 | A | 5/1982 | Goldenberg |
| 5,296,347 | A | 3/1994 | LaMotte, III |
| 5,589,384 | A * | 12/1996 | Lipscombe et al. ..... 435/252.33 |
| 2010/0028356 | A1 | 2/2010 | Schofield et al. |
| 2011/0171687 | A1 | 7/2011 | Schellenberger et al. |

FOREIGN PATENT DOCUMENTS

| EP | 2402754 | * | 1/2012 | ............ G01N 33/53 |
| WO | WO 91/11465 | | 8/1991 | |

(Continued)

OTHER PUBLICATIONS

Janeway et al., Immunobiology 1997, 2:19-2:21.*
Howard et al., Basic Methods in Antibody Production and Characterization. Chapter 6, 2000.*
Mackenzie et al., Dipeptide repeat protein pathology in C9ORF72 mutation cases: clinico-pathological correlations. Acta Neuropathol (2013) 126:859-879.*

(Continued)

*Primary Examiner* — Gregory S Emch
*Assistant Examiner* — Aurora M Fontainhas
(74) *Attorney, Agent, or Firm* — Fish & Richardson P.C.

(57) ABSTRACT

This document provides methods and materials for detecting C9ORF72 hexanucleotide (GGGGCC) (SEQ ID NO: 3) repeat expansion positive (C9+) frontotemporal lobar degeneration or C9+ amyotrophic lateral sclerosis. For example, methods and materials related to using anti-(GP)$_8$ (SEQ ID NO: 2) antibodies to identify mammals (e.g., humans) having C9+ FTLD or C9+ ALS are provided.

17 Claims, 7 Drawing Sheets

(56) References Cited

FOREIGN PATENT DOCUMENTS

| WO | WO2008095261 A1 | 8/2008 |
|---|---|---|
| WO | WO 2013/030588 | 3/2013 |
| WO | WO 2013/036833 | 3/2013 |
| WO | WO 2013/041577 | 3/2013 |
| WO | WO2014114303 A1 | 7/2014 |

OTHER PUBLICATIONS

Mori et al., The C9orf72 GGGGCC Repeat Is Translated into Aggregating Dipeptide-Repeat Proteins in FTLD/ALS. Science vol. 339 Mar. 15, 2013, 1335-1338.*

Ash et al., Unconventional Translation of C9ORF72 GGGGCC Expansion Generates Insoluble Polypeptides Specific to c9FTD/ALS. Neuron 77, 639-646, Feb. 20, 2013.*

International Search Report and Written Opinion in International Application No. PCT/US2014/012801, mailed May 29, 2014, 7 pages.

Barbas and Lerner, "Combinatorial Immunoglobulin Libraries on the Surface of Phage (Phabs): Rapid Selection of Antigen-Specific Fabs," Methods: a Companion to Methods in Enzymology, 1991, 2(2):119-124.

Boeve et al., "Characterization of frontotemporal dementia and/or amyotrophic lateral sclerosis associated with the GGGGCC repeat expansion in C9ORF72," Brain, 2012, 135:765-783.

Boxer et al., "Clinical, neuroimaging and neuropathological features of a new chromosome 9p-linked FTD-ALS family," J Neurol Neurosurg Psychiatry, 2011, 82:196-203.

Carter et al., "Humanization of an anti-p185HER2 antibody for human cancer therapy," Proc. Nat'l. Acad. Sci. USA, 1992, 89:4285-9.

Ciotti et al., "Triplet repeat primed PCR (TP PCR) in molecular diagnostic testing for Friedreich ataxia," J Mol Diagn., 6(4):285-289, Nov. 2004.

Coligan et al. Current Protocols in Immunology, 1997, sections 2.8.1, 2.8.10, 2.10.1, 2.10.4, 4 pages.

Coligan et al., Production of Polyclonal Antisera in Rabbits, Rats, Mice and Hamsters, in Current Protocols in Immunology, 1992, sections 2.4.1, 2.5.1, 2.6.7, 2.7.1, 2.7.12, 2.9.1 and 2.9.3, 8 pages.

Coligan, et al., Unit 9, Current Protocols in Immunology, Wiley Interscience, 1994, 4 pages.

Cossée et al., "Analysis of FRDA patients with interrupted GAA expansions in the frataxin gene by fluorescent triplet primed PCR," Eur J Hum Genet., 9(Suppl):403, 2001.

DeJesus-Hernandez et al., "Expanded GGGGCC Hexanucleotide Repeat in Noncoding Region of C9ORF72 causes Chromosome 9p-Linked FTD and ALS," Neuron, 2011, 72:1-12.

Georghiou et al., "A simple, fast, low-cost screening method for the detection of (GAA)n repeat expansions in Friedreich's ataxia," Eur J Hum Genet., 2001, 9(Suppl 1):303.

Giordana et al., "Dementia and cognitive impairment in amyotrophic lateral sclerosis: a review," Neurol. Sci., 2011, 32:9-16.

Graff-Radford and Woodruff, "Frontotemporal dementia," Neurol., 2007, 27:48-57.

Green and Manson, "Production of Polyclonal Antisera," in Immunochemical Protocols (Manson, ed.), pp. 1 5 (Humana Press 1992).

Green et al., "Antigen-specific human monoclonal antibodies from mice engineered with human Ig heavy and light chain YACs," Nature Genet., 1994, 7:13-21.

Greene et al., "Anti-Proline-Glycine-Proline or Antielastin Autoantibodies are not Evident in Chronic Inflammatory Lung Disease," Am J Respir Crit Case Med., 2010, 181:31-35.

Harlow et al., Antibodies: A Laboratory Manual, (Cold Spring Harbor Pub. 1988) (Table of Contents), 10 pages.

Jones et al., "Replacing the complementarity-determining regions in a human antibody with those from a mouse," Nature, 1986, 321:522-5.

Kobayahi et al., "Expansion of Intronic GGCCTG Hexanucleotide Repeat in NOP56 Causes SCA36, a Type of Spinocerebellar Ataxia Accompanied by Motor Neuron Involvement," Am J Hum Gene., Jul. 2011, 89:121-130.

Kohler & Milstein, "Continuous cultures of fused cells secreting antibody of predefined specificity," Nature, 1975, 256:495-7.

Laaksovirta et al., "Chromosome 9p21 in amyotrophic lateral sclerosis in Finland: a genome-wide association study," Lancet Neurol., 2010, 9:978-85.

Lomen-Hoerth et al., "Are amyotrophic lateral sclerosis patients cognitively normal?," Neurology, 2003, 60:1094-1097.

Lomen-Hoerth et al., "The overlap of amyotrophic lateral sclerosis and frontotemporal dementia," Neurology, 2002, 59:1077-1079.

Lonberg et al., "Antigen-specific human antibodies from mice comprising four distinct genetic modifications," Nature, 1994, 368:856-9.

Losman et al., "Baboon anti-idiotype antibodies mimic a carcinoembryonic antigen epitope," Int. J. Cancer, 1990, 46:310-4.

Mackenzie et al., "Nomenclature for neuropathologic subtypes of frontotemporal lobar degeneration: consensus recommendations," Acta Neuropathol., 2009, 117:15-18.

Neumann et al., "Ubiquitinated TDP-43 in frontotemporal lobar degeneration and amyotrophic lateral sclerosis," Science, 2006, 314:130-133.

Nisonhoff et al., "Separation of univalent fragments from the bivalent rabbit antibody molecule by reduction of disulfide bonds," Arch. Biochem. Biophys., 1960, 89:230-44.

Orlandi et al., "Cloning immunoglobulin variable domains for expression by the polymerase chain reaction," Proc. Nat'l. Acad. Sci. USA, 1989, 86:3833-7.

Pearson, "Repeat Associated Non-ATG Translation Initiation: One DNA, Two Transcripts, Seven Reading Frames, Potentially Nine Toxic Entities!" PLoS Genet., Mar. 2011, 7(3):e1002018, 5 pages.

Phukan et al., "Cognitive impairment in amyotrophic lateral sclerosis," Lancet Neurol., 2007, 6:994-1003.

Porter, "The hydrolysis of rabbit y-globulin and antibodies with crystalline papain," Biochem. J., 1959, 73:119-26.

Riechmann et al., "Reshaping human antibodies for therapy," Nature, 1988, 332:323-7.

Rollinson et al., "Frontotemporal lobar degeneration genome wide association study replication confirms a risk locus shared with amyotrophic lateral sclerosis," Neurobiol Aging, 2011, 21:758.e1-758.e7.

Sandhu, "Protein engineering of antibodies," Crit. Rev. Biotech., 1992, 12:437-62.

Singer et al., "Optimal humanization of 1B4, an anti-CD18 murine monoclonal antibody, is achieved by correct choice of human V-region framework sequences," J. Immunol., 1993, 150:2844-57.

Taylor et al., "Human immunoglobulin transgenes undergo rearrangement, somatic mutation and class switching in mice that lack endogenous IgM," Int. Immunol., 1994, 6:579-91.

van Es et al., "Genome-wide association study identifies 19p13.3 (UNC13A) and 9p21.2 as susceptibility loci for sporadic amyotrophic lateral sclerosis," Nature Genetics, Oct. 2009, 41(10):1083-1088.

Verhoeyen et al., "Reshaping human antibodies: grafting an antilysozyme activity," Science, 1988, 239:1534-6.

Warner et al., "A general method for the detection of large CAG repeat expansions by fluorescent PCR," J Med Genet., Dec. 1996, 33(12):1022-1026.

Winter et al., "Making antibodies by phage display technology," Ann. Rev. Immunol., 1994, 12:433-55.

Zu et al., "Non-ATG—initiated translation directed by microsatellite expansions," PNAS Jan. 2011, 108(1):260-265.

Mann et al., "Dipeptide repeat proteins are present in the p62 positive inclusions in patients with frontotemporal lobar degeneration and motor neurone disease associated with expansions in C9ORF72," Acta Neuropathol Commun., 1:68, Oct. 14, 2013.

European Search Report for Application No. 14743115.9, dated Jul. 7, 2016, 10 pages.

* cited by examiner

METHODS AND MATERIALS FOR DETECTING C9ORF72 HEXANUCLEOTIDE REPEAT EXPANSION POSITIVE FRONTOTEMPORAL LOBAR DEGENERATION OR C9ORF72 HEXANUCLEOTIDE REPEAT EXPANSION POSITIVE AMYOTROPHIC LATERAL SCLEROSIS

CROSS-REFERENCE TO RELATED APPLICATIONS

This application claims the benefit of U.S. Provisional Application Ser. No. 61/756,318, filed Jan. 24, 2013. The disclosure of the prior application is considered part of (and is incorporated by reference in) the disclosure of this application.

SEQUENCE LISTING

The instant application contains a Sequence Listing which has been submitted electronically in ASCII format and is hereby incorporated by reference in its entirety. Said ASCII copy, created on Jan. 23, 2014, is named SEQ.txt and is 7,275 bytes in size.

BACKGROUND

1. Technical Field

This document relates to methods and materials for detecting C9ORF72 hexanucleotide (GGGGCC) (SEQ ID NO: 3) repeat expansion positive (C9$^+$) frontotemporal lobar degeneration (FTLD) or C9$^+$ amyotrophic lateral sclerosis (ALS). For example, this document provides methods and materials related to using anti-(GP)$_8$ (SEQ ID NO: 2) antibodies to identify mammals (e.g., humans) having C9$^+$ FTLD or C9$^+$ ALS.

2. Background Information

FTD and ALS are both devastating neurological diseases. FTD is the second most common cause of pre-senile dementia in which degeneration of the frontal and temporal lobes of the brain results in progressive changes in personality, behavior, and language with relative preservation of perception and memory (Graff-Radford and Woodruff, *Neurol.*, 27:48-57 (2007)). ALS affects 2 in 100,000 people and has traditionally been considered a disorder in which degeneration of upper and lower motor neurons gives rise to progressive spasticity, muscle wasting, and weakness. However, ALS is increasingly recognized to be a multisystem disorder with impairment of frontotemporal functions such as cognition and behavior in up to 50% of patients (Giordana et al., *Neurol. Sci.*, 32:9-16 (2011); Lomen-Hoerth et al., *Neurology*, 59:1077-1079 (2003); and Phukan et al., *Lancet Neurol.*, 6:994-1003 (2007)). Similarly, as many as half of FTD patients develop clinical symptoms of motor neuron dysfunction (Lomen-Hoerth et al., *Neurology*, 60:1094-1097 (2002)). The concept that FTD and ALS represent a clinicopathological spectrum of disease is strongly supported by the recent discovery of the transactive response DNA binding protein with a molecular weight of 43 kD (TDP-43) as the pathological protein in the vast majority of ALS cases and in the most common pathological subtype of FTD (Neumann et al., *Science*, 314:130-133 (2006)), now referred to as frontotemporal lobar degeneration with TDP-43 pathology (FTLD-TDP; Mackenzie et al., *Acta Neuropathol.*, 117:15-18 (2009)).

SUMMARY

This document provides methods and materials for detecting C9$^+$ FTLD or C9$^+$ ALS. For example, this document provides methods and materials related to using anti-(GP)$_8$ (SEQ ID NO: 2) antibodies to identify mammals (e.g., humans) having C9$^+$ FTLD or C9$^+$ ALS. As described herein, biological samples obtained from C9$^+$ FTLD and C9$^+$ ALS patients can contain detectable levels or elevated levels of polyGP polypeptides generated from the expanded hexanucleotide (GGGGCC) (SEQ ID NO: 3) repeat in a noncoding region of C9ORF72 present within the C9$^+$ FTLD or C9$^+$ ALS patient, and antibodies generated against polyGP polypeptides (e.g., antibodies generated against C-Ahx-GPGPGPGPGPGPGPGP-amide; SEQ ID NO:1) can be used to detect those detectable or elevated levels of polyGP polypeptides within biological samples, thereby identifying the patient as having C9$^+$ FTLD or C9$^+$ ALS.

Having the ability to identify mammals having C9$^+$ FTLD or C9$^+$ ALS using the methods and materials provided herein can allow clinicians to differentiate between those patients having C9$^+$ FTLD and those patients having C9$^-$ FTLD and to differentiate between those patients having C9$^+$ ALS and those patients having C9$^-$ ALS in a quick and efficient manner without using nucleic acid amplification techniques. For example, an immunoassay involving the use of an anti-(GP)$_8$ (SEQ ID NO: 2) antibody and a biological sample from a mammal to be tested (e.g., a human patient suspected of having FTLD or ALS) can be used to detect the presence of a detectable or elevated level of polyGP polypeptides that is indicative of C9$^+$ FTLD or C9$^+$ ALS, thereby indicating that the mammal being tested has C9$^+$ FTLD or C9$^+$ ALS. In some cases, an immunological assay involving the use of an anti-(GP)$_8$ (SEQ ID NO: 2) antibody and a biological sample from a mammal to be tested (e.g., a human patient suspected of having FTLD or ALS) can be used to detect the absence of a detectable or elevated level of polyGP polypeptides that is indicative of C9$^-$ FTLD or C9$^+$ ALS, thereby indicating that the mammal being tested has C9$^-$ FTLD or C9$^-$ ALS or does not have FTLD or ALS.

C9$^-$ as used herein refers to the absence of an expanded hexanucleotide (GGGGCC) (SEQ ID NO: 3) repeat in the noncoding region of both C9ORF72 alleles. C9$^+$ as used herein refers to the presence of an expanded hexanucleotide (GGGGCC) (SEQ ID NO: 3) repeat in the noncoding region of at least one C9ORF72 allele. Healthy humans generally can have between about 2 and about 30 hexanucleotide (GGGGCC) (SEQ ID NO: 3) repeats in the noncoding region of C9ORF72. A hexanucleotide (GGGGCC) (SEQ ID NO: 3) repeat in the noncoding region of C9ORF72 is considered expanded when there are more than about 30 hexanucleotide (GGGGCC) (SEQ ID NO: 3) repeats present. For example, a hexanucleotide (GGGGCC) (SEQ ID NO: 3) repeat in the noncoding region of C9ORF72 is considered expanded when there are between about 30 and about 2000 hexanucleotide (GGGGCC) (SEQ ID NO: 3) repeats present (e.g., between about 30 and about 1900, between about 30 and about 1800, between about 30 and about 1700, between about 30 and about 1600, between about 30 and about 1500, between about 30 and about 1400, between about 30 and about 1300, between about 30 and about 1200, between about 30 and about 1100, between about 30 and about 1000, or between about 30 and about 750 hexanucleotide (GGGGCC) (SEQ ID NO: 3) repeats present). In some cases, a hexanucleotide (GGGGCC) (SEQ ID NO: 3) repeat in the noncoding region of C9ORF72 is considered expanded when there are between about 30 and about 5000 or more hexanucleotide (GGGGCC) (SEQ ID NO: 3) repeats present (e.g., between about 30 and about 5000, between about 30 and about 4500, between about 30 and about 4000, between about 30 and about 3500, between about 30 and about 3000, or between about 30 and about 2500 hexanucleotide (GGGGCC) (SEQ ID NO: 3) repeats present).

This document also provides anti-(GP)$_8$ (SEQ ID NO: 2) antibody preparations. As described herein, an anti-(GP)$_8$ (SEQ ID NO: 2) antibody preparation can be a preparation that includes one or more anti-(GP)$_8$ (SEQ ID NO: 2) antibodies having the ability to bind a (GP)$_8$ (SEQ ID NO: 2) polypeptide (GPGPGPGPGP-GPGPGP; SEQ ID NO:2). In some cases, an anti-(GP)$_8$ (SEQ ID NO: 2) antibody of an anti-(GP)$_8$ (SEQ ID NO: 2) antibody preparation provided herein can bind to a (GP)$_8$ (SEQ ID NO: 2) polypeptide with no detectable binding to a (PGP)$_8$ (SEQ ID NO: 4) polypeptide or to a collagen polypeptide. For example, an anti-(GP)$_8$ (SEQ ID NO: 2) antibody preparation provided herein can include anti-(GP)$_8$ (SEQ ID NO: 2) antibodies that bind to a (GP)$_8$ (SEQ ID NO: 2) polypeptide with no detectable binding to a (PGP)$_8$ (SEQ ID NO: 4) polypeptide. Examples of anti-(GP)$_8$ (SEQ ID NO: 2) antibodies having the ability to bind to a (GP)$_8$ (SEQ ID NO: 2) polypeptide with no detectable binding to a (PGP)$_8$ (SEQ ID NO: 4) polypeptide include, without limitation, antibodies generated against C-Ahx-GPGPGPGPGPGPGPGP-amide (SEQ ID NO:1). Anti-(GP)$_8$ (SEQ ID NO: 2) antibody preparations provided herein can be used to identify mammals having C9$^+$ FTLD or C9$^+$ ALS. For example, anti-(GP)$_8$ (SEQ ID NO: 2) antibody preparations provided herein can be used to identify humans having C9$^+$ FTLD or can be used to bind to polypeptides having eight or more (e.g., from 8 to 2000, from 8 to 1900, from 8 to 1800, from 8 to 1700, from 8 to 1600, from 8 to 1500, from 8 to 1000, from 8 to 750, from 8 to 500, from 8 to 250, from 8 to 200, from 8 to 150, from 8 to 100, from 8 to 75, from 8 to 50, or from 8 to 25) GP repeats. In some cases, an anti-(GP)$_8$ (SEQ ID NO: 2) antibody preparations provided herein can be used to detect a polypeptide having a (GP)$_{8-2000}$ amino acid sequence.

In general, one aspect of this document features a method for identifying a mammal having an expanded hexanucleotide (GGGGCC) (SEQ ID NO: 3) repeat in a noncoding region of at least one C9ORF72 allele. The method comprises, or consists essentially of, (a) contacting a biological sample obtained from the mammal with an anti-polyGP antibody under conditions wherein a polyGP polypeptide present within the biological sample and the anti-polyGP antibody form a polyGP polypeptide/anti-polyGP antibody complex, (b) detecting the polyGP polypeptide/anti-polyGP antibody complex, and (c) classifying the mammal as having the expanded hexanucleotide (GGGGCC) (SEQ ID NO: 3) repeat. The mammal can be a human. The biological sample can be a cerebrospinal fluid sample. The biological sample can be a blood sample. The binding affinity of the anti-polyGP antibody for a (GP)$_8$ (SEQ ID NO: 2) polypeptide can be between $10^6$ mol$^{-1}$ and $10^{12}$ mol$^{-1}$. The binding affinity of the anti-polyGP antibody for a (GP)$_8$ (SEQ ID NO: 2) polypeptide can be between $10^6$ mol$^{-1}$ and $10^{12}$ mol$^{-1}$, and the binding affinity of the anti-polyGP antibody for a (PGP)$_8$ (SEQ ID NO: 4) polypeptide can be less than $10^3$ mol$^{-1}$.

In another aspect, this document features a method for identifying a human as having a C9$^+$ neurological condition. The method comprises, or consists essentially of, (a) contacting a biological sample obtained from a human with an anti-polyGP antibody under conditions wherein a polyGP polypeptide present within the biological sample and the anti-polyGP antibody form a polyGP polypeptide/anti-polyGP antibody complex, (b) detecting the polyGP polypeptide/anti-polyGP antibody complex, and (c) classifying the human as having a C9$^+$ neurological condition. The biological sample can be a cerebrospinal fluid sample. The biological sample can be a blood sample. The binding affinity of the anti-polyGP antibody for a (GP)$_8$ (SEQ ID NO: 2) polypeptide can be between $10^6$ mol$^{-1}$ and $10^{12}$ mol$^{-1}$. The binding affinity of the anti-polyGP antibody for a (GP)$_8$ (SEQ ID NO: 2) polypeptide can be between $10^6$ mol$^{-1}$ and $10^{12}$ mol$^{-1}$, and the binding affinity of the anti-polyGP antibody for a (PGP)$_8$ (SEQ ID NO: 4) polypeptide can be less than $10^3$ mol$^{-1}$. The C9$^+$ neurological condition can be C9$^+$ FTLD. The C9$^+$ neurological condition can be C9$^+$ ALS.

In another aspect, this document features an anti-polyGP antibody. The binding affinity of the anti-polyGP antibody for a (GP)$_8$ (SEQ ID NO: 2) polypeptide can be between $10^6$ mol$^{-1}$ and $10^{12}$ mol$^{-1}$. The binding affinity of the anti-polyGP antibody for a (GP)$_8$ (SEQ ID NO: 2) polypeptide can be between $10^6$ mol$^{-1}$ and $10^{12}$ mol$^{-1}$, and wherein the binding affinity of the anti-polyGP antibody for a (PGP)$_8$ (SEQ ID NO: 4) polypeptide can be less than $10^3$ mol$^{-1}$. The anti-polyGP antibody can be an anti-(GP)$_8$ (SEQ ID NO: 2) antibody.

In another aspect, this document features an antibody preparation comprising an anti-polyGP antibody. The binding affinity of the anti-polyGP antibody for a (GP)$_8$ (SEQ ID NO: 2) polypeptide can be between $10^6$ mol$^{-1}$ and $10^{12}$ mol$^{-1}$. The binding affinity of the anti-polyGP antibody for a (GP)$_8$ (SEQ ID NO: 2) polypeptide can be between $10^6$ mol$^{-1}$ and $10^{12}$ mol$^{-1}$, and the binding affinity of the anti-polyGP antibody for a (PGP)$_8$ (SEQ ID NO: 4) polypeptide can be less than $10^3$ mol$^{-1}$. The anti-polyGP antibody can be an anti-(GP)$_8$ (SEQ ID NO: 2) antibody.

In another aspect, this document features a method for detecting a polyGP polypeptide present within the sample. The method comprises, or consists essentially of, (a) contacting the biological sample with an anti-polyGP antibody under conditions wherein the polyGP polypeptide present within the sample and the anti-polyGP antibody form a polyGP polypeptide/anti-polyGP antibody complex, and (b) detecting the polyGP polypeptide/anti-polyGP antibody complex, thereby detecting the presence of the polyGP polypeptide within the sample. The biological sample can be a cerebrospinal fluid sample. The biological sample can be a blood sample. The binding affinity of the anti-polyGP antibody for a (GP)$_8$ (SEQ ID NO: 2) polypeptide can be between $10^6$ mol$^{-1}$ and $10^{12}$ mol$^{-1}$. The binding affinity of the anti-polyGP antibody for a (GP)$_8$ (SEQ ID NO: 2) polypeptide can be between $10^6$ mol$^{-1}$ and $10^{12}$ mol$^{-1}$, and the binding affinity of the anti-polyGP antibody for a (PGP)$_8$ polypeptide can be less than $10^3$ mol$^{-1}$. The anti-polyGP antibody can be a monoclonal antibody.

In another aspect, this document features a method for detecting the presence or absence of a polyGP polypeptide within the sample. The method comprises, or consists essentially of, (a) contacting the biological sample with an anti-polyGP antibody under conditions wherein the polyGP polypeptide, if present within the sample, and the anti-polyGP antibody form a polyGP polypeptide/anti-polyGP antibody complex, and (b) determining the presence or absence of the polyGP polypeptide/anti-polyGP antibody complex from step (a), wherein the presence of the complex indicates the presence of the polyGP polypeptide within the sample, and wherein the absence of the complex indicates the absence of the polyGP polypeptide within the sample. The biological sample can be a cerebrospinal fluid sample. The biological sample can be a blood sample. The binding affinity of the anti-polyGP antibody for a $(GP)_8$ polypeptide can be between $10^6$ $mol^{-1}$ and $10^{12}$ $mol^{-1}$. The binding affinity of the anti-polyGP antibody for a $(GP)_8$ (SEQ ID NO: 2) polypeptide can be between $10^6$ $mol^{-1}$ and $10^{12}$ $mol^{-1}$, and the binding affinity of the anti-polyGP antibody for a $(PGP)_8$ (SEQ ID NO: 4) polypeptide can be less than $10^3$ $mol^{-1}$. The anti-polyGP antibody can be a monoclonal antibody.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 discloses SEQ ID NOS 14-21, respectively, in order of appearance.

DETAILED DESCRIPTION

Figure 1:
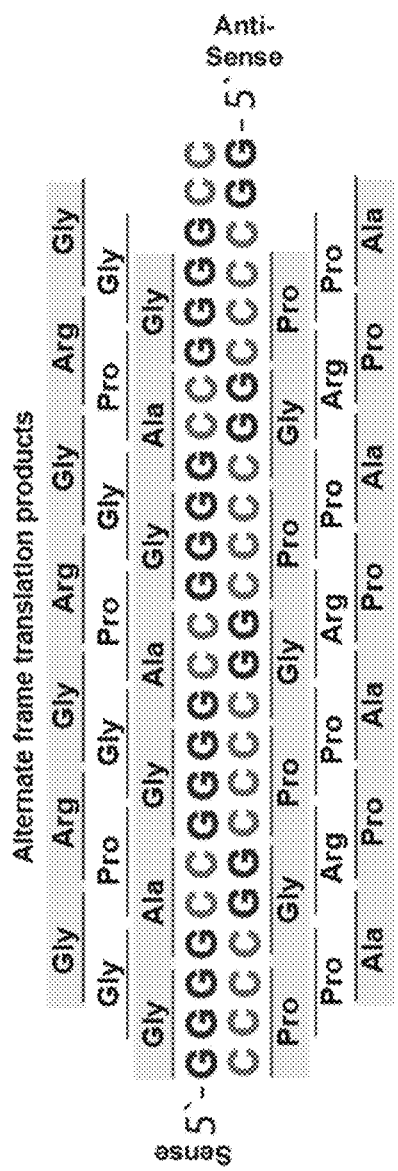
FIG. 1 is a schematic of translation products of the three alternate frames of the sense RNA transcript generated from the expanded C9ORF72 GGGGCC (SEQ ID NO: 3) repeat that would generate repeating dipeptides of (Glycine-Alanine)$_n$, (Glycine-Proline)$_n$, and (Glycine-Arginine)$_n$, and the translation products of the three alternate frames of the anti-sense RNA GGCCCC (SEQ ID NO: 5) repeat that would generate repeating dipeptides of (Proline-Alanine)$_n$, (Proline-Glycine)$_n$, and (Proline-Arginine)$_n$.

This document provides methods and materials for detecting C9$^+$ FTLD or C9$^+$ ALS. For example, this document provides methods and materials related to using anti-$(GP)_8$ (SEQ ID NO: 2) antibodies to identify mammals (e.g., humans) having C9$^+$ FTLD or C9$^+$ ALS. As described herein, biological samples obtained from C9$^+$ FTLD and C9$^+$ ALS patients can contain detectable levels or elevated levels of polyGP polypeptides generated from the expanded hexanucleotide (GGGGCC) (SEQ ID NO: 3) repeat in a noncoding region of C9ORF72 present within the C9$^+$ FTLD or C9$^+$ ALS patient, and antibodies generated against polyGP polypeptides (e.g., antibodies generated against C-Ahx-GPGPGPGPGPGPGPGP-amide; SEQ ID NO:1) can be used to detect those detectable or elevated levels of polyGP polypeptides within biological samples, thereby identifying the patient as having C9$^+$ FTLD or C9$^+$ ALS.

Any appropriate mammal can be assessed for C9+ FTLD or C9+ ALS or can be assessed for the presence of an expanded hexanucleotide (GGGGCC) (SEQ ID NO: 3) repeat in a noncoding region of C9ORF72 as described herein. For example, humans, non-human primates, monkeys, horses, cows, sheep, pigs, dogs, and cats can be assessed for the presence of an expanded hexanucleotide (GGGGCC) (SEQ ID NO: 3) repeat in a noncoding region of C9ORF72 using anti-polyGP polypeptide antibodies such as the MC001 antibody. In some cases, a human diagnosed as having FTLD or ALS can be assessed for the presence of an expanded hexanucleotide (GGGGCC) (SEQ ID NO: 3) repeat in a noncoding region of C9ORF72 using an anti-polyGP polypeptide antibody as described herein.

When assessing a mammal for detectable levels or elevated levels of polyGP polypeptides generated from an expanded hexanucleotide (GGGGCC) (SEQ ID NO: 3) repeat in a noncoding region of C9ORF72, any appropriate sample can be evaluated. For example, tissue samples, cerebrospinal fluid samples, or blood samples can be obtained from a mammal and tested to determine the level of polyGP polypeptides.

Any appropriate method can be used to assess the level of polyGP polypeptides within a sample. For example, immunological assays such as Western blots, FACS analyses, ELISAs, and RIAs can be used to determine whether or not a sample contains a detectable level or elevated level of polyGP polypeptides generated from an expanded hexanucleotide (GGGGCC) (SEQ ID NO: 3) repeat in a noncoding region of C9ORF72.

In immunological assays, an antibody having specific binding affinity for a polyGP polypeptide (e.g., a $(GP)_8$ (SEQ ID NO: 2) polypeptide or the MC001 antibody) or a secondary antibody that binds to such an antibody can be labeled, either directly or indirectly. Suitable labels include, without limitation, radionuclides (e.g., $^{125}I$, $^{131}I$, $^{35}S$, $^3H$, $^{32}P$, $^{33}P$, or $^{14}C$), fluorescent moieties (e.g., fluorescein, FITC, PerCP, rhodamine, or PE), luminescent moieties (e.g., Qdot™ nanoparticles supplied by Invitrogen (Carlsbad, Calif.)), compounds that absorb light of a defined wavelength, or enzymes (e.g., alkaline phosphatase or horseradish peroxidase). Antibodies can be indirectly labeled by conjugation with biotin and then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting polyGP polypeptides generated from an expanded hexanucleotide (GGGGCC) (SEQ ID NO: 3) repeat in a noncoding region of C9ORF72 can be performed in a variety of formats including, without limitation, sandwich assays, competition assays (competitive RIA), or bridge immunoassays. See, for example, U.S. Pat. Nos. 5,296,347; 4,233,402; 4,098,876; and 4,034,074. Methods of detecting polyGP polypeptides generated from an expanded hexanucleotide (GGGGCC) (SEQ ID NO: 3) repeat in a noncoding region of C9ORF72 generally include contacting a biological sample (e.g., a cerebrospinal fluid sample or blood sample) with an antibody that binds to a polyGP polypeptide (e.g., a $(GP)_8$ (SEQ ID NO: 2) polypeptide) and detecting binding of the polyGP polypeptide to the antibody. For example, an antibody having specific binding affinity for a polyGP polypeptide (e.g., a $(GP)_8$ (SEQ ID NO: 2) polypeptide) can be immobilized on a solid substrate by any of a variety of methods known in the art and then exposed to the biological sample. Binding of the polyGP polypeptide to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). In some cases, the antibody can be labeled and detected as described above. A standard curve using known quantities of a polyGP polypeptide can be generated to aid in the quantitation of the levels of the polyGP polypeptide within a sample being tested.

The term "antibody" as used herein refers to intact antibodies as well as antibody fragments that retain some ability to bind an epitope. Such fragments include, without limitation, Fab, F(ab')2, and Fv antibody fragments. The term "epitope" refers to an antigenic determinant on an antigen to which the paratope of an antibody binds. Epitopic determinants usually consist of chemically active surface groupings of molecules (e.g., amino acid or sugar residues) and usually have specific three dimensional structural characteristics as well as specific charge characteristics.

The antibodies provided herein can be any antibody (e.g., a monoclonal or polyclonal antibody) having specific binding affinity for a polyGP polypeptide (e.g., a $(GP)_8$ (SEQ ID NO: 2) polypeptide). In some cases, an anti-polyGP polypeptide antibody (e.g., an anti-$(GP)_8$ (SEQ ID NO: 2) polypeptide antibody) provided herein can have little or no detectable binding to a $(PGP)_8$ (SEQ ID NO: 4) polypeptide or to a collagen polypeptide (e.g., a human collagen polypeptide). In some cases, the binding affinity of an anti-polyGP polypeptide antibody (e.g., an anti-$(GP)_8$ (SEQ ID NO: 2) polypeptide antibody) provided herein for a polyGP polypeptide (e.g., a $(GP)_8$ (SEQ ID NO: 2) polypeptide) can be greater than $10^3$ $mol^{-1}$ (e.g., greater than $10^3$, $10^4$, $10^5$, $10^6$, $10^7$, $10^8$, $10^9$, $10^{10}$, $10^{11}$, $10^{12}$, or $10^{13}$ $mol^{-1}$). In some cases, the binding affinity of an anti-polyGP polypeptide antibody (e.g., an anti-$(PG)_8$ polypeptide antibody) provided herein for a polyGP polypeptide (e.g., a $(GP)_8$ (SEQ ID NO: 2) polypeptide) can be between $10^3$ $mol^{-1}$ and $10^{13}$ $mol^{-1}$ (e.g., between $10^3$ $mol^{-1}$ and $10^{12}$ $mol^{-1}$, between $10^3$ $mol^{-1}$ and $10^{11}$ $mol^{-1}$, between $10^3$ $mol^{-1}$ and $10^{10}$ $mol^{-1}$, between $10^3$ $mol^{-1}$ and $10^9$ $mol^{-1}$, between $10^3$ $mol^{-1}$ and $10^8$ $mol^{-1}$, between $10^3$ $mol^{-1}$ and $10^7$ $mol^{-1}$, between $10^4$ $mol^{-1}$ and $10^{12}$ $mol^{-1}$, between $10^5$ $mol^{-1}$ and $10^{12}$ $mol^{-1}$, between $10^6$ $mol^{-1}$ and $10^{12}$ $mol^{-1}$, between $10^7$ $mol^{-1}$ and $10^{12}$ $mol^{-1}$, between $10^8$ $mol^{-1}$ and $10^{12}$ $mol^{-1}$, between $10^9$ $mol^{-1}$ and $10^{12}$ $mol^{-1}$, between $10^{10}$ $mol^{-1}$ and $10^{12}$ $mol^{-1}$, or between $10^6$ $mol^{-1}$ and $10^{10}$ $mol^{-1}$). In some cases, the binding affinity of an anti-polyGP polypeptide antibody (e.g., an anti-$(GP)_8$ (SEQ ID NO: 2) polypeptide antibody) provided herein for a $(PGP)_8$ (SEQ ID NO: 4) polypeptide or to a collagen polypeptide (e.g., a human collagen polypeptide) can be less than $10^5$ $mol^{-1}$ binding affinity (e.g., less than $10^4$, $10^3$, or $10^2$ $mol^{-1}$).

Antibodies provided herein can be prepared using any appropriate method. For example, a polyGP polypeptide preparation or a substantially pure $(GP)_8$ (SEQ ID NO: 2) polypeptide (e.g., C-Ahx-GPGPGPGPGPGPGPGP-amide (SEQ ID NO: 1)) can be used as an immunogen to elicit an immune response in an animal such that specific antibodies are produced. In some cases, tagged (e.g., GST-tagged) or untagged polypeptides having a $(GP)_{8-2000}$ sequence can be used as an immunogen to elicit an immune response in an animal such that specific antibodies are produced. The immunogen used to immunize an animal can be chemically synthesized or derived from translated cDNA. For example, polypeptides having a $(GP)_{8-2000}$ sequence can be expressed exogenously by cells (e.g., mammalian or bacteria cells) and isolated or used as a crude polypeptide extract. In some cases, the immunogen can be conjugated to a carrier polypeptide, if desired. Commonly used carriers that are chemically coupled to an immunizing polypeptide include, without limitation, m-maleimidobenzoyl-N-hydroxysuccinimide ester (MBS), keyhole limpet hemocyanin (KLH), thyroglobulin, bovine serum albumin (BSA), and tetanus toxoid.

The preparation of polyclonal antibodies is well-known to those skilled in the art. See, e.g., Green et al., Production of Polyclonal Antisera, in IMMUNOCHEMICAL PROTOCOLS (Manson, ed.), pages 1 5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan, et al., Unit 9, Current Protocols in Immunology, Wiley Interscience, 1994).

The preparation of monoclonal antibodies also is well-known to those skilled in the art. See, e.g., Kohler & Milstein, *Nature* 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS 1N MOLECULAR BIOLOGY, VOL. 10, pages 79 104 (Humana Press 1992).

In addition, methods of in vitro and in vivo multiplication of monoclonal antibodies are well known to those skilled in the art. Multiplication in vitro can be carried out in suitable culture media such as Dulbecco's Modified Eagle Medium or RPMI 1640 medium, optionally replenished by mammalian serum such as fetal calf serum, or trace elements and growth sustaining supplements such as normal mouse peritoneal exudate cells, spleen cells, and bone marrow macrophages. Production in vitro provides relatively pure antibody preparations and allows scale up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells (e.g., osyngeneic mice) to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

In some cases, the antibodies provided herein can be made using non-human primates. General techniques for raising therapeutically useful antibodies in baboons can be found, for example, in Goldenberg et al., International Patent Publication WO 91/11465 (1991) and Losman et al., *Int. J. Cancer,* 46:310 (1990).

In some cases, the antibodies can be humanized monoclonal antibodies. Humanized monoclonal antibodies can be produced by transferring mouse complementarity determining regions (CDRs) from heavy and light variable chains of the mouse immunoglobulin into a human variable domain, and then substituting human residues in the framework regions of the murine counterparts. General techniques for cloning murine immunoglobulin variable domains are described, for example, by Orlandi et al., *Proc. Nat'l. Acad. Sci. USA* 86:3833 (1989). Techniques for producing humanized monoclonal antibodies are described, for example, by Jones et al., *Nature* 321:522 (1986); Riechmann et al., *Nature* 332:323 (1988); Verhoeyen et al., *Science* 239:1534 (1988); Carter et al., *Proc. Nat'l. Acad. Sci. USA* 89:4285 (1992); Sandhu, *Crit. Rev. Biotech.* 12:437 (1992); and Singer et al., *J. Immunol.* 150:2844 (1993).

Antibodies provided herein can be derived from human antibody fragments isolated from a combinatorial immunoglobulin library. See, for example, Barbas et al., METHODS: A COMPANION TO METHODS IN ENZYMOLOGY, VOL. 2, page 119 (1991) and Winter et al., *Ann. Rev. Immunol.* 12: 433 (1994). Cloning and expression vectors that are useful for producing a human immunoglobulin phage library can be obtained, for example, from STRATAGENE Cloning Systems (La Jolla, Calif.).

In some cases, antibodies provided herein can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immunol.* 6:579 (1994).

Antibody fragments can be prepared by proteolytic hydrolysis of an intact antibody or by the expression of a nucleic acid encoding the fragment. Antibody fragments can be obtained by pepsin or papain digestion of intact antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. In some cases, an enzymatic cleavage using pepsin can be used to produce two monovalent Fab' fragments and an Fc fragment directly. These methods are described, for example, by Goldenberg (U.S. Pat. Nos. 4,036,945 and 4,331,647). See also Nisonhoff et al., *Arch. Biochem. Biophys.* 89:230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1 2.8.10 and 2.10.1 2.10.4.

Other methods of cleaving antibodies, such as separation of heavy chains to form monovalent light heavy chain fragments, further cleavage of fragments, or other enzymatic, chemical, or genetic techniques may also be used provided the fragments retain some ability to bind (e.g., selectively bind) its epitope.

The antibodies provided herein can be substantially pure. The term "substantially pure" as used herein with reference to an antibody means the antibody is substantially free of other polypeptides, lipids, carbohydrates, and nucleic acid with which it is naturally associated. Thus, a substantially pure antibody is any antibody that is removed from its natural environment and is at least 60 percent pure. A substantially pure antibody can be at least about 65, 70, 75, 80, 85, 90, 95, or 99 percent pure.

In some cases, biological samples obtained from C9$^+$ FTLD and C9$^+$ ALS patients can contain detectable levels or elevated levels of polyGA polypeptides, polyGR polypeptides, polyPA polypeptides, and/or polyPR polypeptides in addition to polyGP polypeptides generated from the expanded hexanucleotide (GGGGCC) (SEQ ID NO: 3) repeat in a noncoding region of C9ORF72 present within the C9$^+$ FTLD or C9$^+$ ALS patient. In such cases, antibodies generated against polyGA polypeptides (e.g., antibodies generated against C-Ahx-GAGAGAGAGAGAGAGA-amide (SEQ ID NO: 6)), or a GST-tagged (GA)$_{50}$ polypeptide that was exogenously expressed in bacteria and isolated), antibodies generated against polyGR polypeptides (e.g., antibodies generated against C-Ahx-GRGRGRGRGR-GRGRGR-amide (SEQ ID NO: 7)), or a GST-tagged (GR)$_{50}$ polypeptide that was exogenously expressed in bacteria and isolated), antibodies generated against polyPA polypeptides (e.g., antibodies generated against C-Ahx-PAPAPAPAPA-PAPAPA-amide (SEQ ID NO: 12)), or a GST-tagged (PA)$_{50}$ polypeptide that was exogenously expressed in bacteria and isolated), and/or antibodies generated against polyPR polypeptides (e.g., antibodies generated against C-Ahx-PRPRPRPRPRPRPRPR-amide (SEQ ID NO: 13)) or a GST-tagged (PR)$_{50}$ polypeptide that was exogenously expressed in bacteria and isolated) can be used instead of or in combination with antibodies generated against polyGP polypeptides (e.g., antibodies generated against C-Ahx-GPGPGPGPGPGPGPGP-amide; SEQ ID NO:1) as described herein to detect those detectable or elevated levels of polyGA polypeptides, polyGR polypeptides, polyPA polypeptides, polyPR polypeptides, and/or polyGP polypeptides within biological samples, thereby identifying the patient as having C9$^+$ FTLD or C9$^+$ ALS. In addition, the anti-polyGA polypeptide antibodies (e.g., antibodies generated against C-Ahx-GAGAGAGAGAGAGAGA-amide (SEQ ID NO: 6)), anti-polyGR polypeptide antibodies (e.g., antibodies generated against C-Ahx-GRGRGRGRGRGR-GRGR-amide (SEQ ID NO: 7)), anti-polyPA polypeptide antibodies (e.g., antibodies generated against C-Ahx-PAPA-PAPAPAPAPAPA-amide (SEQ ID NO: 12)), and anti-polyPR polypeptide antibodies (e.g., antibodies generated against C-Ahx-PRPRPRPRPRPRPRPR-amide (SEQ ID NO: 13)) provided herein can be made and used using methods similar to those described herein with respect to the anti-polyGP polypeptide antibodies.

The invention will be further described in the following example, which does not limit the scope of the invention described in the claims.

EXAMPLE

Example 1

Producing a Preparation Containing Anti-polyGP Polypeptide Antibodies

The expansion of a hexanucleotide (GGGGCC) (SEQ ID NO: 3) repeat in a noncoding region of C9ORF72 was hypothesized to form an mRNA sense transcript with the capability of expressing polyGA polypeptides, polyGP polypeptides, and polyGR polypeptides (FIG. 1). To test this hypothesis, a polyclonal antibody preparation was produced as follows.

Briefly, two rabbits were immunized by injection with a mixture of the following polypeptides: C-Ahx-GAGAGA-GAGAGAGAGA-amide (SEQ ID NO: 6), C-Ahx-GPGPG-PGPGPGPGPGP-amide (SEQ ID NO: 1), and C-Ahx-GR-GRGRGRGRGRGRGR-amide (SEQ ID NO: 7). Prior to immunization of the rabbits, the purity of each polypeptide was verified by mass spectrometry, and each polypeptide was conjugated to m-maleimidobenzoyl-N-hydroxysuccinimide ester (MBS) as an immune carrier. Repeat immunizations were performed, and bleeds were subsequently collected to obtain antiserum.

Figure 2:
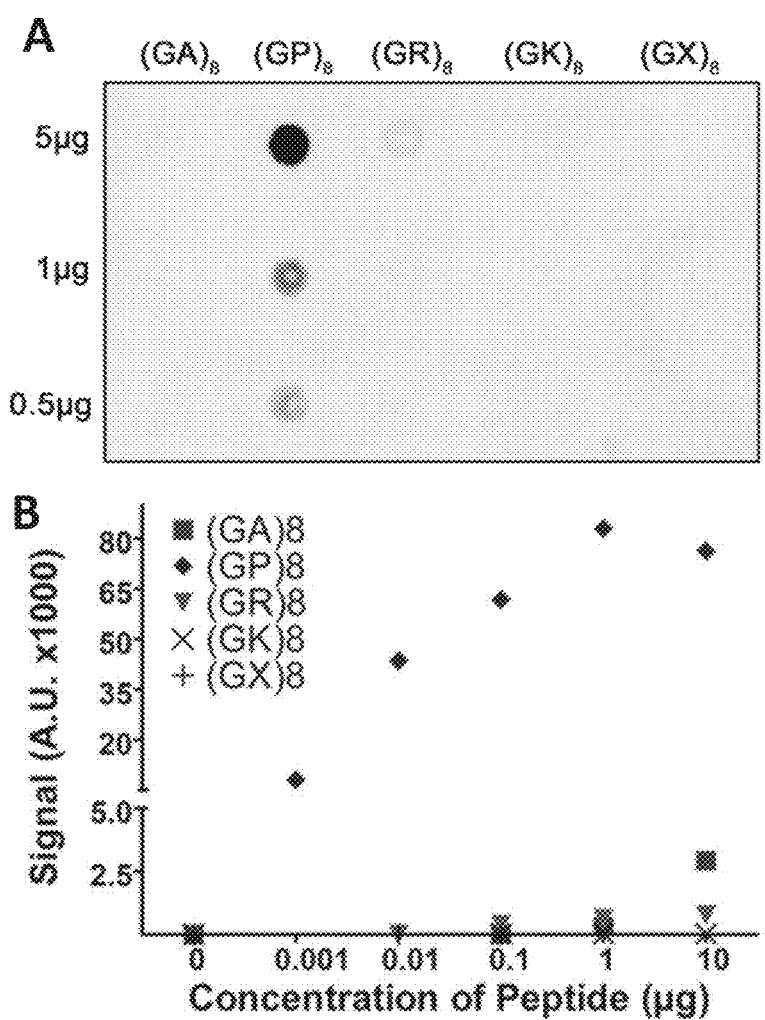
FIG. 2A is a photograph of a dot blot demonstrating that MC-001 antibody (a polyclonal antibody raised in rabbits against a mixture of C-Ahx-GAGAGAGAGAGAGAGA-amide (SEQ ID NO: 6), C-Ahx-GPGPGPGPGPGPGPGP-amide (SEQ ID NO: 1), and C-Ahx-GRGRGRGRGRGRGRGR-amide (SEQ ID NO: 7)) exhibits high affinity for the $(GP)_8$ (SEQ ID NO: 2) polypeptide as compared to a $(GA)_8$ (SEQ ID NO: 8) polypeptide, a $(GR)_8$ (SEQ ID NO: 9) polypeptide, a $(GK)_8$ (SEQ ID NO: 10) polypeptide, or a $(GX)_8$ (SEQ ID NO: 11) polypeptide ("X" represents a random amino acid that is not glycine, alanine, proline, arginine, cysteine, valine, or lysine). The unconjugated $(GP)_8$ (SEQ ID NO: 2) polypeptides, $(GA)_8$ (SEQ ID NO: 8) polypeptides, $(GR)_8$ (SEQ ID NO: 9) polypeptides, $(GK)_8$ (SEQ ID NO: 10) polypeptides, and $(GX)_8$ (SEQ ID NO: 11) polypeptides were dotted onto a nitrocellulose membrane at the amounts shown and probed with 100 ng/mL of the MC-001 antibody.
FIG. 2B is a graph plotting the binding signal (relative absorbance units; A.U.) of 500 ng/mL of the MC-001 antibody to unconjugated $(GP)_8$ (SEQ ID NO: 2) polypeptides, $(GA)_8$ (SEQ ID NO: 8) polypeptides, $(GR)_8$ (SEQ ID NO: 9) polypeptides, $(GK)_8$ (SEQ ID NO: 10) polypeptides, and $(GX)_8$ (SEQ ID NO: 11) polypeptides as detected using the Meso Scale Discovery (MSD™) platform.
Figure 3:
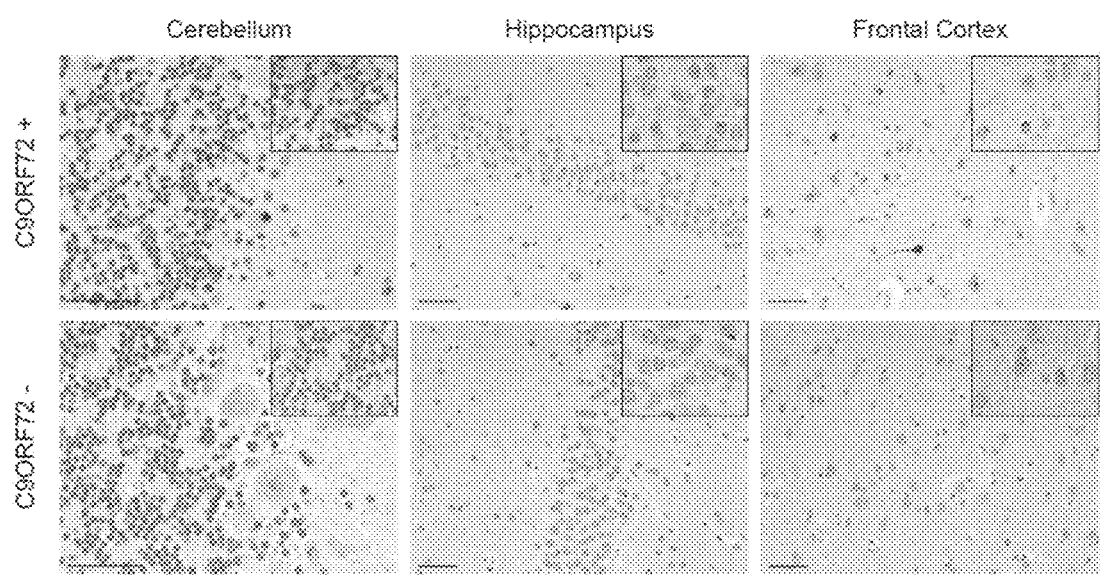
FIG. 3 contains photographs of the indicated tissues from C9$^+$ FTLD (C9ORF72+) and C9$^-$ FTLD (C9ORF72−) patients stained with the MC-001 antibody. The MC-001 antibody detected inclusions in cerebellar granule and Purkinjie cells throughout hippocampus proper and dentate fascia and in the frontal cortex of C9$^+$ FTLD patients, but not in C9$^-$ FTLD patients.
Figure 5:
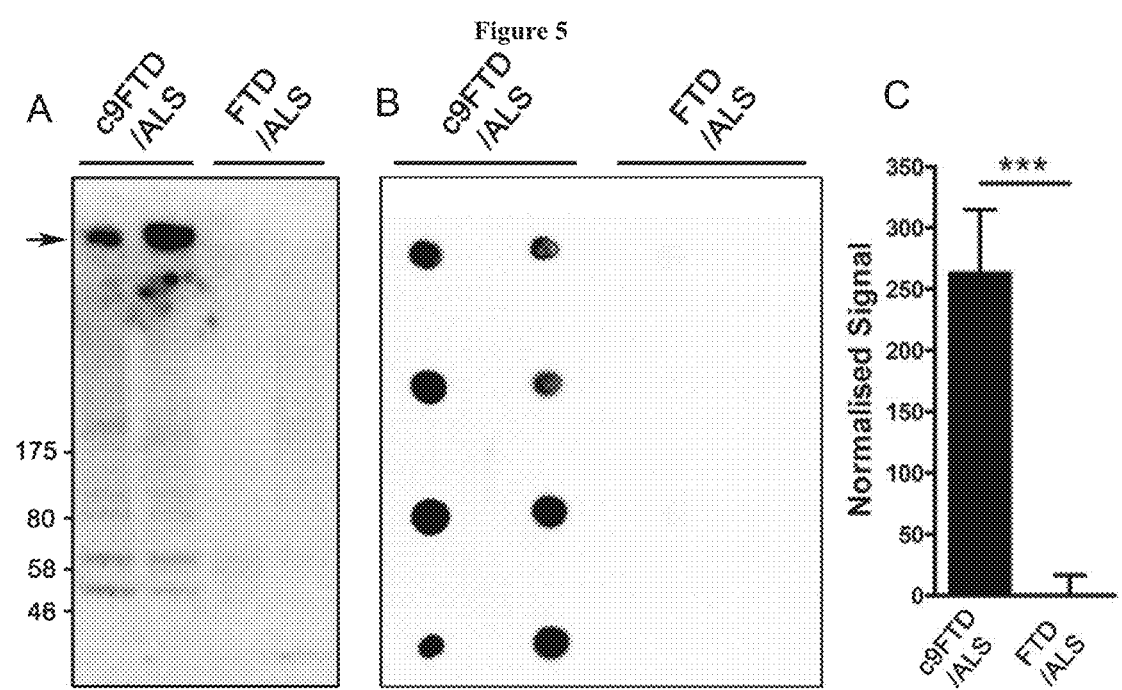
FIG. 5A is a photograph of an immunoblot of a urea fraction from a sequential extraction of cerebellar tissue using 100 ng/mL of the MC-001 antibody.
FIG. 5B is a photograph of a dot blot of 2 µL urea fractions blotted onto a nitrocellulose membrane and probed with 50 ng/mL of the MC-001 antibody.
FIG. 5C is a graph plotting the levels of insoluble material detected in the urea fraction using the MSD™ platform and the MC-001 antibody (t-test; P=0.0004).

Antiserum was directly used for some experimental investigations, such as immunohistochemical analysis of C9ORF72 translated polypeptides in human brain sections (FIG. 3 and FIG. 5). In addition, polyclonal antibodies were purified from the antiserum with Protein A or Protein G. This generated a pool of antibodies that preferentially detect polyGP polypeptides (FIG. 2). The polyclonal antibody preparation produced was designated the MC-001 antibody.

The MC-001 antibody bound to (GP)$_8$ (SEQ ID NO: 2) polypeptides, and not (GA)$_8$ (SEQ ID NO: 8) polypeptides, (GR)$_8$ (SEQ ID NO: 9) polypeptides, (GK)$_8$ (SEQ ID NO: 10) polypeptides, and (GX)$_8$ (SEQ ID NO: 11) polypeptides (FIGS. 2A and 2B).

Example 2

Figure 4:
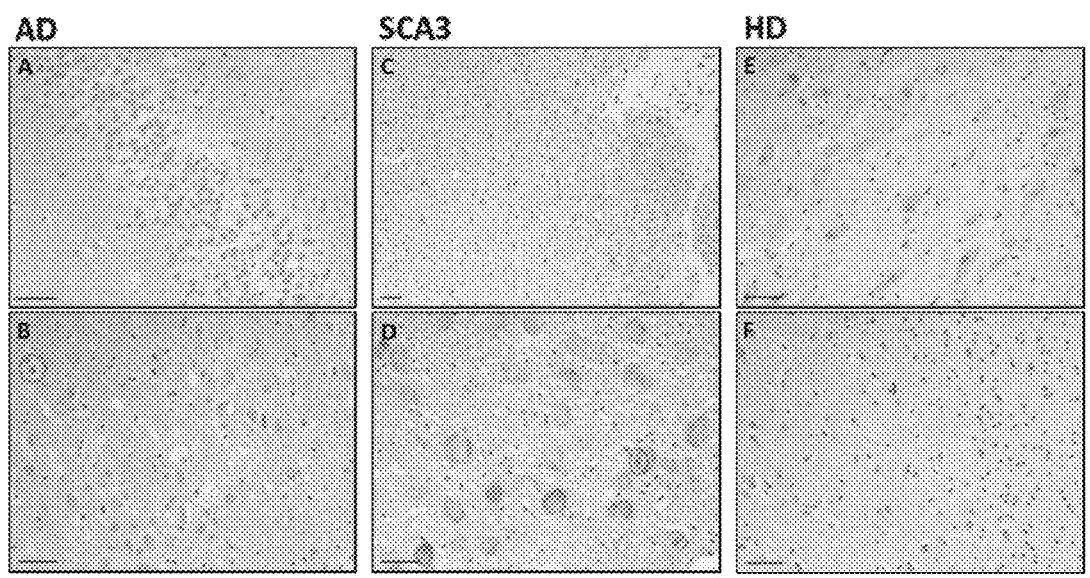
FIGS. 4A-F are photographs of immunohistochemistry using the MC-001 antibody to stain tissue from patients with Alzheimer's disease (A, B), spinocerebellar ataxia type 3 (C, D), and Huntington's disease (E, F). Dentate fascia (A) and hippocampus proper (B) of the Alzheimer's disease patient exhibited no MC-001 antibody immunoreactivity. Pontine nucleus (C) and locus ceruleus (D) of the spinocerebellar ataxia type 3 patient exhibited non-specific diffuse nuclear staining and melanin in the cytoplasm (a natural pigment of the neurons of this nucleus). Basal forebrain nucleus of Meynert (E) and putamen (F) of the Huntington's disease patient exhibited non-specific diffuse nuclear staining.

Anti-polyGP Polypeptide Antibodies are Capable of Detecting C9$^+$ FLTD and C9$^+$ ALS Patients The MC-001 antibody was capable of specific detection of insoluble inclusions of polyGP polypeptides in the brains of patients with the C9ORF72 GGGGCC (SEQ ID NO: 3) genetic expansion. Cerebellar, hippocampal, and frontocortical sections exhibited specific MC-001 immunoreactivity by immunohistochemistry in FTLD patients with the genetic GGGGCC (SEQ ID NO: 3) expansion (FIG. 3), but not in sections from FTLD patients without the genetic expansion. No MC-001 immunoreactivity was detected in brain tissue sections from affected areas of Alzheimer's disease (AD) or the trinucleotide repeat disorders spinocerebellar ataxia type 3 (SCA3) or Huntington's disease (HD) (FIG. 4). These results indicate that MC-001 antibody immunoreactivity can be highly specific only to patients with the C9ORF72 GGGGCC (SEQ ID NO: 3) genetic expansion.

Sequential extraction of protein from the cerebellum of C9$^+$FTD or C9$^+$ALS cases with increasingly stringent detergents revealed that the MC-001 antibody labeled insoluble high molecular weight material. Immunoblots of the 7M urea fractions from cerebellar tissue revealed the presence of MC-001 immunoreactive material that, due to its large size and insolubility, became trapped in the top of the SDS-PAGE stacking gel (FIG. 5A). To assess MC-001 immunoreactivity, dot-blot (FIG. 5B) and MSD immunoassay (FIG. 5C) were conducted to overcome the problem of the immobility of the material by SDS-PAGE. The presence of high molecular weight insoluble material in C9+ FTD/ALS brain was comparable to other neurodegenerative disorders with insoluble neuronal inclusions such as insoluble tau inclusions in Alzheimer's disease. The MC-001 antibody only exhibited immunoreactivity to insoluble material extracted from brain regions from patients with the C9ORF72 GGGGCC (SEQ ID NO: 3) genetic expansion.

Example 3

Figure 6:
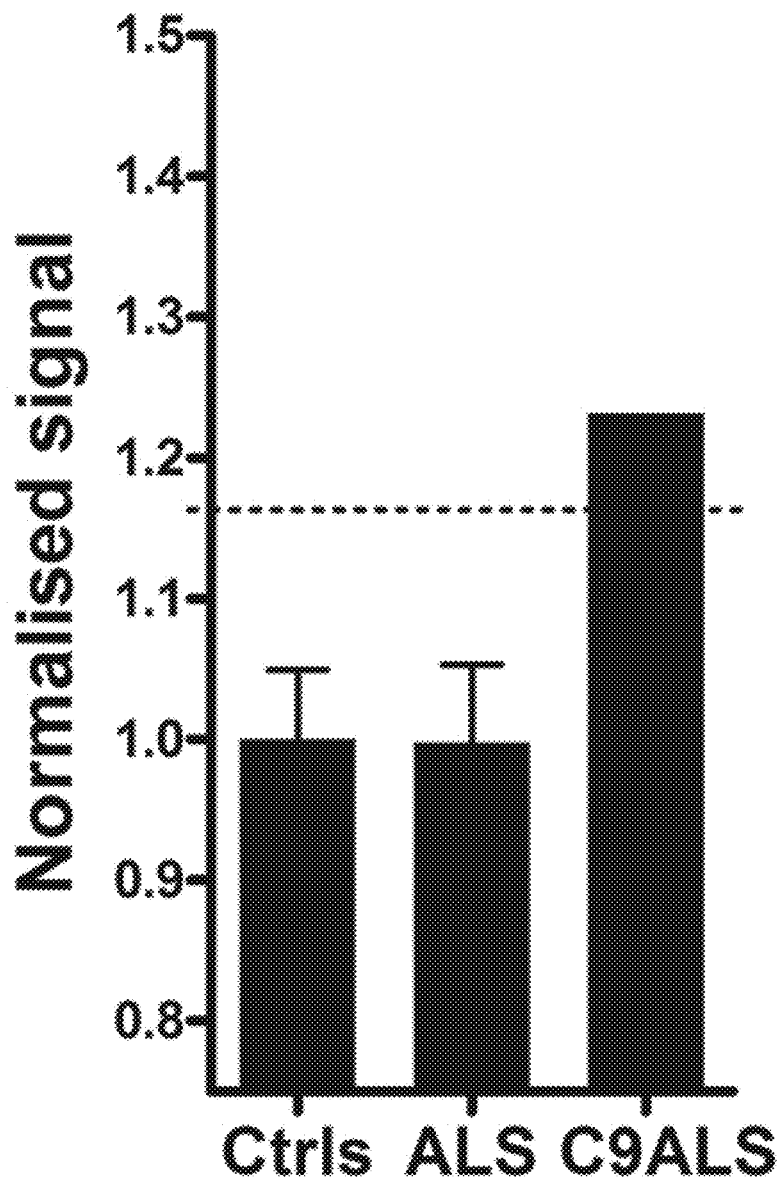
FIG. 6 is a bar graph plotting the normalized binding signal of the MC-001 antibody to poly(GP) polypeptides present in cerebral spinal fluid (CSF) from control patients (CLT), C9$^-$ ALS patients, and a C9$^+$ ALS patient. To measure anti-poly(GP) polypeptide immunoreactivity in CSF obtained from healthy controls (CTL, n=2), C9$^-$ ALS patients (ALS, n=6), and an ALS patient with the C9ORF72 mutation (C9$^+$ ALS, n=1), 90 µL of CSF was adsorbed to carbon electrodes at the bottom of a 96-well MSD™ assay plate. After immobilization and blocking, the MC-001 antibody in combination with a Sulfo-tagged rabbit secondary antibody was added to wells. Immunoreactivity was measured by adding MSD™1x Read Buffer to wells and reading the light emission at 620 nm after electrochemical stimulation using the MSD™ Sector Imager 2400.

Anti-polyGP Polypeptide Antibodies are Capable of Detecting C9+ ALS Patients Using Cerebrospinal Fluid To evaluate the potential of the MC-001 antibody further, cerebrospinal fluid from two normal controls, six ALS patients negative for C9ORF72 expanded repeats, and one C9+ ALS patient was assessed using the MSD platform. As shown in FIG. 6, MC-001 immunoreactivity in the C9+ ALS CSF was increased more than threefold the standard error of the mean signal in CSF from control ALS patients (indicated by dashed line). These results demonstrate that the presence of polypeptides such as polyGP polypeptides in patient cerebrospinal fluid can serve as a detectable marker for both diagnostic and prognostic tests for C9+ FTD and ALS.

Example 4

Producing Goat Anti-polyGP Antibodies

One goat was immunized by injection with a C-Ahx-GPGPGPGPGPGPGPGP-amide (SEQ ID NO: 1) polypeptide. Prior to immunization, the purity of the polypeptide was verified by mass spectrometry, and the polypeptide was conjugated to m-maleimidobenzoyl-N-hydroxysuccinimide ester (MBS) as an immune carrier. Repeat immunizations were performed, and bleeds were subsequently collected to obtain antiserum. Subsequent antibody purification by Protein A or Protein G, or antigen-specific purification, was performed.

Example 5

Producing Rabbit Anti-polyGP Antibodies

Two rabbits were immunized by injection with a C-Ahx-GPGPGPGPGPGPGPGP-amide (SEQ ID NO: 1) polypeptide. Prior to immunization, the purity of the polypeptide was verified by mass spectrometry, and the polypeptide was conjugated to m-maleimidobenzoyl-N-hydroxysuccinimide ester (MBS) as an immune carrier. Repeat immunizations are performed, and bleeds are subsequently collected to obtain antiserum. Subsequent antibody purification by Protein A or Protein G, or antigen-specific purification, is performed.

Example 6

Producing Rabbit Anti-polyGA Antibodies

Two rabbits were immunized by injection with a C-Ahx-GAGAGAGAGAGAGAGA-amide (SEQ ID NO: 6) polypeptide. Prior to immunization, the purity of the polypeptide was verified by mass spectrometry, and the polypeptide was conjugated to m-maleimidobenzoyl-N-hydroxysuccinimide ester (MBS) as an immune carrier. Repeat immunizations were performed, and bleeds were subsequently collected to obtain antiserum. Subsequent antibody purification by Protein A or Protein G, or antigen-specific purification, was performed.

Two rabbits were immunized by injection with recombinant $(GA)_{50}$ tagged with glutatione S-transferase (GST). In brief, synthetic cDNA encoding $(GA)_{50}$ was inserted into a pGEX-6P-1 vector (GE Healthcare) downstream of the GST sequence, and the plasmid was transfected into Rosetta™ (DE3)pLysS Competent Cells (EMD4Biosciences). For induction of recombinant GST-$(GA)_{50}$ polypeptide, bacteria were cultured overnight in the presence of isopropyl β-D-1-thiogalactopyranoside. Cells were then lysed, sonicated, and centrifuged at 18000×g for 30 minutes. The resulting supernatant was applied to a Glutathione Sepharose 4B column, and the recombinant GST-$(GA)_{50}$ polypeptide was eluted from the column using Tris-Cl (50 mM, pH 8.0) containing 20 mM reduced glutathione. After removal of glutathione from the GST-$(GA)_{50}$ preparation, GST-$(GA)_{50}$ was used for immunization of rabbits.

Repeat immunizations are performed, and bleeds are subsequently collected to obtain antiserum. Subsequent antibody purification by Protein A or Protein G, or antigen-specific purification, is performed.

Example 7

Producing Rabbit Anti-polyGR Antibodies

Two rabbits were immunized by injection with a C-Ahx-GRGRGRGRGRGRGRGR-amide (SEQ ID NO: 7) polypeptide. Prior to immunization, the purity of the polypeptide was verified by mass spectrometry, and the polypeptide was conjugated to m-maleimidobenzoyl-N-hydroxysuccinimide ester (MBS) as an immune carrier. Repeat immunizations are performed, and bleeds are subsequently collected to obtain antiserum. Subsequent antibody purification by Protein A or Protein G, or antigen-specific purification, is performed.

Example 8

Producing Mouse Monoclonal Anti-polyGP Antibodies

Five mice were immunized by injection with a mixture of C-Ahx-GAGAGAGAGAGAGAGA-amide (SEQ ID NO: 6), C-Ahx-GPGPGPGPGPGPGPGP-amide (SEQ ID NO: 1), and C-Ahx-GRGRGRGRGRGRGRGR-amide (SEQ ID NO: 7) polypeptides. Prior to immunization, the purity of the polypeptide was verified by mass spectrometry, and the polypeptide was conjugated to m-maleimidobenzoyl-N-hydroxysuccinimide ester (MBS) as an immune carrier.

B cells were isolated from the spleen of immunized mice and were fused with myeloma cells to create hybridomas. Hybridomas were cultured under conditions which permit growth of only hybridoma cells where each cell produces an antibody against a single epitope. Single hybridoma cells were separated and were grown in distinct wells of a microtiter plate. Each hybridoma was screened to determine whether it produces the desired antibody (i.e., antibody against $(GP)_8$ (SEQ ID NO: 2), $(GA)_8$ (SEQ ID NO: 8), or $(GR)_8$ (SEQ ID NO: 9)). The hybridoma cells producing a desired monoclonal antibody are cultured, and monoclonal antibodies are harvested from the supernatant. Monoclonal antibody purification from the supernatant is performed by affinity purification using Protein A or Protein G, or using immobilized antigen (i.e., (GP)$_8$ (SEQ ID NO: 2), (GA)$_8$ (SEQ ID NO: 8), or (GR)$_8$ (SEQ ID NO: 9) polypeptides).

Antibody clones were tested for the ability to bind (PA)$_8$, (PR)$_8$, (GP)$_8$, (GA)$_8$, or (GR)$_8$ polypeptides. Briefly, (PA)$_8$, (PR)$_8$, (GP)$_8$, (GA)$_8$, and (GR)$_8$ polypeptides were adsorbed individually to carbon electrodes at the bottom of 96-well MSD™ assay plates. After immobilization and blocking, antibodies from individual clones in combination with a Sulfo-tagged rabbit secondary antibody were added to the wells. Immunoreactivity was measured by adding MSD™1x Read Buffer to the wells and reading the light emission at 620 nm after electrochemical stimulation using the MSD™ Sector Imager 2400.

Figure 7:
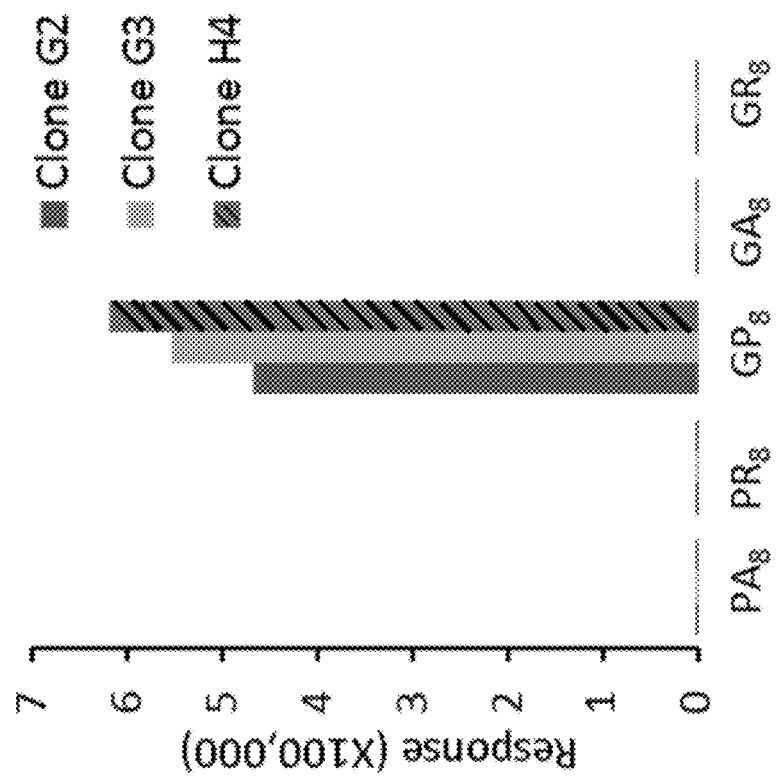
FIG. 7 is a bar graph plotting the binding signals of monoclonal antibody preparations made to detect poly(GP) polypeptides from three different clones to the indicated polypeptides.

Three monoclonal antibody clones (clones G2, G3, and H4) produced monoclonal antibodies that bound to the (GP)$_8$ polypeptide with no detectable binding to the (PA)$_8$, (PR)$_8$, (GA)$_8$, and (GR)$_8$ polypeptides (FIG. 7).

Example 9

Producing Rabbit Anti-polyPA Antibodies

Two rabbits were immunized by injection with the following polypeptide antigen: C-Ahx-PAPAPAPAPAPAPAPA-amide (SEQ ID NO: 12).

Prior to immunization, the polypeptide purity was verified by mass spectrometry, and the polypeptide was conjugated to m-Maleimidobenzoyl-N-hydroxysuccinimide ester (MBS) as an immune carrier. Repeat immunizations are performed, and bleeds are collected to obtain antiserum. Subsequent antibody purification by Protein A or Protein G, or antigen-specific purification, is performed.

Example 10

Producing Rabbit Anti-polyPR Antibodies

Two rabbits were immunized by injection with the following polypeptide antigen: C-Ahx-PRPRPRPRPRPRPRPR-amide (SEQ ID NO: 13).

Prior to immunization, the polypeptide purity was verified by mass spectrometry, and the polypeptide was conjugated to m-Maleimidobenzoyl-N-hydroxysuccinimide ester (MBS) as an immune carrier. Repeat immunizations are performed, and bleeds are collected to obtain antiserum. Subsequent antibody purification by Protein A or Protein G, or antigen-specific purification, is performed.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody preparation comprising anti-polyGP (Glycine-Proline) antibodies, wherein said anti-polyGP antibodies of said preparation are at least about 65 percent pure and comprise a label wherein said label is a radionuclide, fluorescent moiety, luminescent moiety, or an enzyme.

2. The preparation of claim 1, wherein the binding affinity of said anti-polyGP antibodies for a polypeptide consisting of SEQ ID NO: 2 is between $10^6$ mol$^{-1}$ and $10^{12}$ mol$^{-1}$.

3. The preparation of claim 1, wherein the binding affinity of said anti-polyGP antibodies for a polypeptide consisting of SEQ ID NO: 2 is between $10^6$ mol$^{-1}$ and $10^{12}$ mol$^{-1}$, and wherein the binding affinity of said anti-polyGP antibodies for a polypeptide consisting of SEQ ID NO: 4 is less than $10^3$ mol$^{-1}$.

4. The preparation of claim 1, wherein said anti-polyGP antibodies are antibodies to SEQ ID NO: 2.

5. The preparation of claim 1, wherein said anti-polyGP antibodies of said preparation are monoclonal anti-polyGP antibodies.

6. An antibody preparation comprising an anti-polyGP (Glycine-Proline) antibody and a secondary antibody having the ability to bind to said anti-polyGP antibody, wherein said secondary antibody comprises a label, and wherein said label is a radionuclide, fluorescent moiety, luminescent moiety, or an enzyme.

7. The preparation of claim 6, wherein the binding affinity of said anti-polyGP antibody for a polypeptide consisting of SEQ ID NO: 2 is between $10^6$ mol$^{-1}$ and $10^{12}$ mol$^{-1}$.

8. The preparation of claim 6, wherein the binding affinity of said anti-polyGP antibody for a polypeptide consisting of SEQ ID NO: 2 is between $10^6$ mol$^{-1}$ and $10^{12}$ mol$^{-1}$, and wherein the binding affinity of said anti-polyGP antibody for a polypeptide consisting of SEQ ID NO: 4 is less than $10^3$ mol$^{-1}$.

9. The preparation of claim 6, wherein said anti-polyGP antibody is an antibody to SEQ ID NO: 4.

10. The preparation of claim 6, wherein said anti-polyGP antibody of said preparation is a monoclonal antibody to SEQ ID NO: 2.

11. A method for making an antibody preparation comprising anti-polyGP (Glycine-Proline) antibodies, wherein said method comprises:

(a) administering a polyGP polypeptide to a mammal under conditions wherein anti-polyGP antibodies are formed within said mammal, (b) purifying said anti-polyGP antibodies from said mammal to obtain said preparation, wherein said anti-polyGP antibodies of said preparation are at least about 65 percent pure, and (c) labeling said anti-polyGP antibodies of said preparation with a label, wherein said label is a radionuclide, fluorescent moiety, luminescent moiety, or an enzyme.

12. The method of claim 11, wherein said mammal is a mouse.

13. The method of claim 11, wherein the binding affinity of said anti-polyGP antibodies for a polypeptide consisting of SEQ ID NO: 2 is between $10^6$ mol$^{-1}$ and $10^{12}$ mol$^{-1}$.

14. The method of claim 11, wherein the binding affinity of said anti-polyGP antibodies for a polypeptide consisting of SEQ ID NO: 2 is between $10^6$ mol$^{-1}$ and $10^{12}$ mol$^{-1}$, and wherein the binding affinity of said anti-polyGP antibodies for a polypeptide consisting of SEQ ID NO: 4 is less than $10^3$ mol$^{-1}$.

15. A method for making an antibody preparation comprising anti-polyGP (Glycine-Proline) antibodies, wherein said method comprises:

(a) culturing hybridoma cells to form supernatant comprising anti-polyGP antibodies, (b) harvesting anti-polyGP antibodies from said supernatant to form said preparation, wherein said anti-polyGP antibodies of said preparation are at least about 65 percent pure, and (c) labeling said anti-polyGP antibodies of said preparation with a label, wherein said label is a radionuclide, fluorescent moiety, luminescent moiety, or an enzyme.

16. The method of claim 15, wherein the binding affinity of said anti-polyGP antibodies for a polypeptide consisting of SEQ ID NO: 2 is between $10^6$ mol$^{-1}$ and $10^{12}$ mol$^{-1}$.

17. The method of claim 15, wherein the binding affinity of said anti-polyGP antibodies for a polypeptide consisting of SEQ ID NO: 2 is between $10^6$ mol$^{-1}$ and $10^{12}$ mol$^{-1}$, and wherein the binding affinity of said anti-polyGP antibodies for a polypeptide consisting of SEQ ID NO: 4 is less than $10^3$ mol$^{-1}$.

* * * * *

SEQUENCE LISTING

```
<160> NUMBER OF SEQ ID NOS: 21

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ahx
<220> FEATURE:
<223> OTHER INFORMATION: C-term amide

<400> SEQUENCE: 1

Cys Xaa Gly Pro Gly Pro Gly Pro Gly Pro Gly Pro Gly Pro Gly Pro
1               5                   10                  15

Gly Pro

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Pro Gly Pro Gly Pro Gly Pro Gly Pro Gly Pro Gly Pro Gly Pro
1               5                   10                  15

<210> SEQ ID NO 3
<211> LENGTH: 6
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 ggggcc                                                               6

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Gly Pro Pro Gly Pro Pro Gly Pro Pro Gly Pro Pro Gly Pro Pro
1               5                   10                  15

Gly Pro Pro Gly Pro Pro Gly Pro
            20

<210> SEQ ID NO 5
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 ggcccc                                                               6

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ahx
<220> FEATURE:
<223> OTHER INFORMATION: C-term amide

<400> SEQUENCE: 6

Cys Xaa Gly Ala Gly Ala Gly Ala Gly Ala Gly Ala Gly Ala Gly Ala
1               5                   10                  15

Gly Ala

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ahx
<220> FEATURE:
<223> OTHER INFORMATION: C-term amide

<400> SEQUENCE: 7
```

```
Cys Xaa Gly Arg Gly Arg Gly Arg Gly Arg Gly Arg Gly Arg
1               5                   10                  15

Gly Arg

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ala Gly Ala Gly Ala Gly Ala Gly Ala Gly Ala Gly Ala Gly Ala
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Arg Gly Arg Gly Arg Gly Arg Gly Arg Gly Arg Gly Arg Gly Arg
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Lys Gly Lys Gly Lys Gly Lys Gly Lys Gly Lys Gly Lys Gly Lys
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid except Gly, Ala, Pro, Arg, Cys,
      Val or Lys
<220> FEATURE:
<221> NAME/KEY: MOD_RES
<222> LOCATION: (4)..(4)
<223> OTHER INFORMATION: Any amino acid except Gly, Ala, Pro, Arg, Cys,
      Val or Lys
<220> FEATURE:
<221> NAME/KEY: MOD_RES
<222> LOCATION: (6)..(6)
<223> OTHER INFORMATION: Any amino acid except Gly, Ala, Pro, Arg, Cys,
      Val or Lys
<220> FEATURE:
<221> NAME/KEY: MOD_RES
<222> LOCATION: (8)..(8)
<223> OTHER INFORMATION: Any amino acid except Gly, Ala, Pro, Arg, Cys,
      Val or Lys
<220> FEATURE:
<221> NAME/KEY: MOD_RES
<222> LOCATION: (10)..(10)
<223> OTHER INFORMATION: Any amino acid except Gly, Ala, Pro, Arg, Cys,
```

```
      Val or Lys
<220> FEATURE:
<221> NAME/KEY: MOD_RES
<222> LOCATION: (12)..(12)
<223> OTHER INFORMATION: Any amino acid except Gly, Ala, Pro, Arg, Cys,
      Val or Lys
<220> FEATURE:
<221> NAME/KEY: MOD_RES
<222> LOCATION: (14)..(14)
<223> OTHER INFORMATION: Any amino acid except Gly, Ala, Pro, Arg, Cys,
      Val or Lys
<220> FEATURE:
<221> NAME/KEY: MOD_RES
<222> LOCATION: (16)..(16)
<223> OTHER INFORMATION: Any amino acid except Gly, Ala, Pro, Arg, Cys,
      Val or Lys

<400> SEQUENCE: 11

Gly Xaa Gly Xaa Gly Xaa Gly Xaa Gly Xaa Gly Xaa Gly Xaa Gly Xaa
1               5                   10                  15

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ahx
<220> FEATURE:
<223> OTHER INFORMATION: C-term amide

<400> SEQUENCE: 12

Cys Xaa Pro Ala Pro Ala Pro Ala Pro Ala Pro Ala Pro Ala Pro Ala
1               5                   10                  15

Pro Ala

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ahx
<220> FEATURE:
<223> OTHER INFORMATION: C-term amide

<400> SEQUENCE: 13

Cys Xaa Pro Arg Pro Arg Pro Arg Pro Arg Pro Arg Pro Arg Pro Arg
1               5                   10                  15

Pro Arg

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Arg Gly Arg Gly Arg Gly
1               5
```

```
<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Pro Gly Pro Gly Pro Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ala Gly Ala Gly Ala Gly
1               5

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggggccgggg ccggggccgg ggcc                                            24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggccccggcc ccggccccgg cccc                                            24

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Gly Pro Gly Pro Gly Pro
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

```
Pro Arg Pro Arg Pro Arg Pro
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Pro Ala Pro Ala Pro Ala
1               5
```